(12) United States Patent
Chu

(10) Patent No.: US 9,277,988 B1
(45) Date of Patent: Mar. 8, 2016

(54) INTRAOCULAR LENSES WITH QUANTUM DOTS

(71) Applicant: Milton W. Chu, Camarillo, CA (US)

(72) Inventor: Milton W. Chu, Camarillo, CA (US)

( * ) Notice: Subject to any disclaimer, the term of this patent is extended or adjusted under 35 U.S.C. 154(b) by 324 days.

(21) Appl. No.: 13/815,774

(22) Filed: Mar. 15, 2013

(51) Int. Cl.
*A61F 2/16* (2006.01)

(52) U.S. Cl.
CPC ....... *A61F 2/1613* (2013.01); *A61F 2002/1681* (2013.01); *A61F 2250/0097* (2013.01)

(58) Field of Classification Search
USPC ........................................ 623/6.56
See application file for complete search history.

(56) References Cited

U.S. PATENT DOCUMENTS

| | | | |
|---|---|---|---|
| 4,277,852 A | 7/1981 | Poler | |
| 4,738,680 A | 4/1988 | Herman | |
| 4,923,468 A * | 5/1990 | Wild | A61F 2/16 623/6.48 |
| 5,037,435 A | 8/1991 | Change et al. | |
| 5,089,180 A | 2/1992 | Dunks et al. | |
| 5,158,719 A | 10/1992 | Chang et al. | |
| 5,182,053 A | 1/1993 | Creasman et al. | |
| 5,246,634 A | 9/1993 | Ichikawa et al. | |
| 5,252,262 A | 10/1993 | Patel | |
| 5,958,194 A | 9/1999 | Glazier | |
| 6,235,055 B1 | 5/2001 | Chu et al. | |
| 6,447,118 B1 | 9/2002 | Okumura et al. | |
| 6,637,316 B2 | 10/2003 | Engelke et al. | |
| 8,308,800 B2 | 11/2012 | Chu et al. | |
| 2007/0141163 A1 * | 6/2007 | Vitaliano | A61K 9/5169 424/490 |
| 2008/0077238 A1 | 3/2008 | Deacon et al. | |
| 2010/0094414 A1 | 4/2010 | Downer et al. | |
| 2010/0185260 A1 * | 7/2010 | Olson | 607/54 |
| 2011/0264209 A1 * | 10/2011 | Wiechmann | A61F 2/14 623/6.6 |

FOREIGN PATENT DOCUMENTS

WO    WO 2011/127079 A1    10/2011

OTHER PUBLICATIONS

Reed, et al., "Observation of discreet electronic states in a zero-dimensional semiconductor nanostructure", Phys. Rev. Letters, 60: pp. 535-537, (1988).

* cited by examiner

*Primary Examiner* — David H Willse
*Assistant Examiner* — Tiffany Shipmon
(74) *Attorney, Agent, or Firm* — Foley & Lardner LLP

(57) ABSTRACT

Intraocular lenses with quantum dots, materials and methods for making optical lenses, and methods of use are disclosed and claimed. Such lenses provide accurate detectable markers that can be used to align, detect, and correct orientation of lenses prior to, during and after use.

14 Claims, 5 Drawing Sheets

INTRAOCULAR LENSES WITH QUANTUM DOTS

FIELD OF DISCLOSURE

This disclosure relates to improved intraocular lenses for implantation in the eye and improved methods to identify their orientation during and after such implementation.

BACKGROUND

Intraocular lenses (IOLs) can be implanted in the anterior chamber, at the iris plane, in the ciliary suclus space, in the posterior chamber, in the capsular bag, or at other intended spaces inside the eye. Such lenses are used in a variety of surgical procedures such as cataract surgery, clear lensectomy/vision correction, secondary implantation of an intraocular lens, phakic intraocular lens, and other vision correcting procedures.

It is important that intraocular lenses are implanted with the correct orientation, in order for the lens optic to achieve the desired optical result and desired movement. Many intraocular lenses with advanced optical qualities, such as toric optics, require proper orientation and precise alignment to a predetermined ocular axis in order to achieve the intended visual results.

Misalignment can occur at the time of surgery and even after surgery, in the post-operative period due to rotational movements. Misalignment can adversely effect the visual result for the patient.

There are a number of intraocular lenses which are designed to move inside the eye, in order to provide additional optical benefits such as accommodation and enhanced voluntary focusing of vision. These intraocular lenses feature toric optical correction which require precise alignment. Misalignment of the toric correction can create optical problems.

There are also a growing number of multi-focal intraocular lenses which are designed to correct near and intermediate vision so that bifocal or trifocal glasses are not needed. These multi-focal lenses, which can correct astigmatism, need to be aligned precisely with a pre-determined axis of the eye, as well. In the same vein, there are phakic intraocular lenses designed to correct astigmatism, which likewise need to be aligned precisely with a pre-determined axis of the eye, as well.

Currently, intraocular lens manufacturers address the issue of intraocular lens orientation by using design features such as clear round dots, clear lines, holes, notches, and tabs, to signal the proper orientation of the intraocular lens. However, these design features may be difficult to use for several reasons.

First, these design features are small and difficult to see, because they are designed to minimize visual interference with the functions of the eyes. Further, intraocular lenses are typically made out of highly transparent and colorless materials, making these subtle features even more difficult to discern. Further, when a lens is folded and rolled-up in the injector, these design features cannot be identified correctly. Likewise, when the lens is unfolded in an eye with a small pupil, it is frequently difficult or impossible to see the orientation dot, line, notch, hole or tab, because the mark may be hidden behind the iris. After the lens has unfolded, if the iris covers and obscures either a clear or colored orientation mark, the obscured mark is rendered useless.

In U.S. Pat. Nos. 6,235,055 and 8,308,800, the present inventor discloses the use of a colored mark on the haptics of a toric IOL that helps to mark the axis of the IOL. These patents also suggest the use of bi-color marks to aid in the anterior and posterior orientation of the intraocular lenses.

The current IOLs also lack suitable marks indicating the magnitude for optical correction. Toric optical corrections have a magnitude known in diopters which can range from 0.25 to 6.0 diopters or greater. It would be useful to have a method of marking to reflect this information. Currently, there is not such method of marking.

SUMMARY

One embodiment of the present disclosure provides an intraocular lens comprising (a) a central lens optic and (b) a mark disposed on the central lens optic or on a haptic projecting outwardly from the central lens optic, the mark comprising a plurality of nano-sized particles of semi-conductor nanocrystals, defined as quantum dots.

In some embodiments, the quantum dots, when stimulated, produce an emission wavelength of between 300 nm and 2,000 nm. In some embodiments, the quantum dots, when stimulated, produce an emission wavelength between 750 nm and 2000 nm. In some embodiments, the quantum dots, when stimulated, produce an emission wavelength between 600 nm and 749 nm. In some embodiments, the quantum dots, when stimulated, produce an emission wavelength of between 561 nm and 599 nm. In some embodiments, the quantum dots, when stimulated, produce an emission wavelength of between 500 nm and 560 nm. In some embodiments, the quantum dots, when stimulated, produce an emission wavelength of between 400 nm and 499 nm. In some embodiments, the quantum dots, when stimulated, produce an emission wavelength of between 300 nm and 399 nm.

In some embodiments, the mark comprises two or more different kinds of quantum dots which have different stimulated emission wavelengths.

In some embodiments, the mark is disposed in a pattern selected from the group consisting of dots, lines, circles, triangles, bars, letters and numbers.

In some embodiments, the mark further comprises one or more color pigments. In some embodiments, the one or more color pigments are selected from the group consisting of copper phthalocyanine, violet dye, green dye, and titanium dioxide.

In some embodiments, the mark is disposed on the haptic.

Also provided, in one embodiment, is a method of detecting the intraocular lens according to claim 1, comprising detecting stimulated emission of the quantum dots by a microscope and/or a CCD, CMOS and/or Indium Gallium Arsenide solid state camera.

Further provided, in one embodiment, is a method of using the intraocular lens of the present disclosure, the method comprising: identifying the orientation of the intraocular lens with stimulated emission wavelength from the quantum dots; and under guidance of the identified orientation, implanting the intraocular lens to the correct location and/or orientation in an eye; and/or adjusting the location and/or position of a previously implanted intraocular lens when needed.

Provided, in one embodiment, is a method of using the intraocular lens of the present disclosure, comprising identifying parameters about the intraocular lens based on stimulated emission spectrum from the quantum dots.

Also provided is a method of preparing the intraocular lens of the present disclosure, comprising micro-deposition of a layer containing quantum dots filled uncured polymer to the surface of an intraocular lens and then polymerizing that marking layer.

Also provided is a method of making the intraocular lens of the present disclosure, comprising micro-deposition of a layer of quantum dots filled uncured polymer to a micro-depression in an intraocular lens and then polymerizing that marking layer.

BRIEF DESCRIPTION OF THE DRAWINGS

Provided as embodiments of this disclosure are drawings which illustrate by exemplification only, and not limitation, wherein.

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION

The following description serves to illustrate the present disclosure. The description or the examples included therein are in no way intended to limit the scope of the disclosure.

The present disclosure, in some embodiments, provides an intraocular lens comprising (a) a central lens optic and (b) a mark disposed on the central lens optic or on a haptic projecting outwardly from the central lens optic. The mark includes a plurality of nano-sized particles of semi-conductor nanocrystals, known as quantum dots. These quantum dots can emit light visible by eyes or detectable by sensors, when stimulated. The mark that includes these quantum dots, if disposed at a sufficient number to enable detection by eyes or by a sensor and at a location and/or in a shape suitable to indicate the orientation or location of the lens, can be used to identify the orientation and/or location of the lens.

Quantum Dots

"Quantum dots" are semiconductors in the form of nano-sized crystals whose electronic characteristics are closely related to the size and shape of the individual crystal (Reed et al. (1988) Phys Rev Lett., 60 (6): 535-7). A quantum dot has its excitons confined in all three spatial dimensions.

Quantum dots emit light due to activity of excitons or bound electrons and their electron holes. These emissions under natural outdoor sunlight or normal indoor light are generally of faint intensity that they are barely visible to the unaided eye. When quantum dots are exposed to a "stimulating wavelength," however, they produce a strong emission light. The "stimulated" emission wavelength can lie in the ultraviolet (UV), visible, near infrared (NIR), or shortwave infrared (SWIR) spectrum.

Figure 1A:
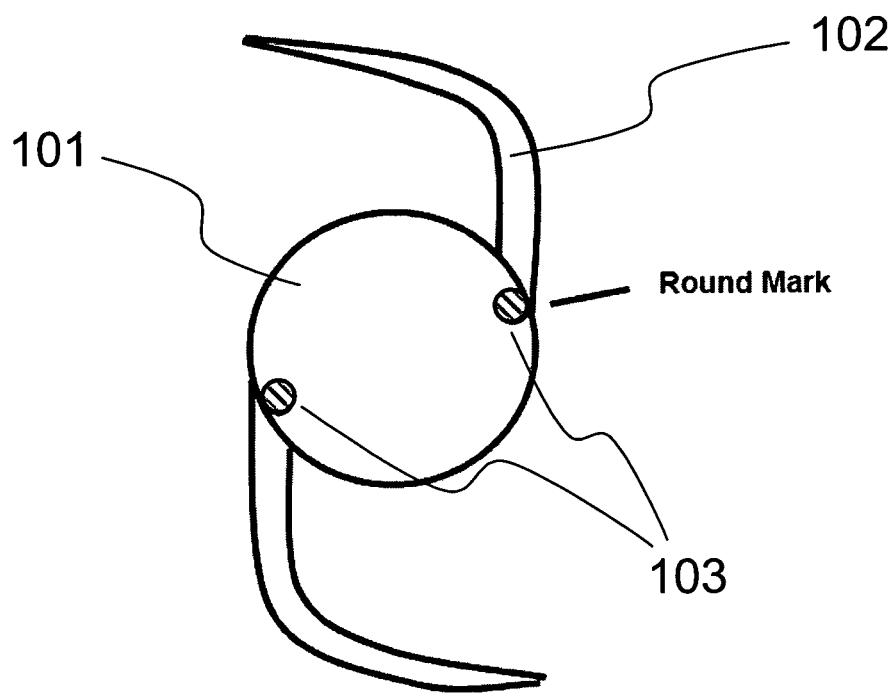
FIG. 1A-B depict an intraocular lens two round marks containing quantum dots with a "stimulating" frequency of 400 nm and an emission frequency of 750 nm. Under exposure to outdoor sunlight and/or indoor lighting, the round marks have a slight pinkish color (shown as shaded) which is not fluorescent (FIG. 1A). The marks have a strong reddish color (shown as dark circles) which is fluorescent in both the visible spectrum and invisible NIR spectrum (FIG. 1B)
Figure 1B:
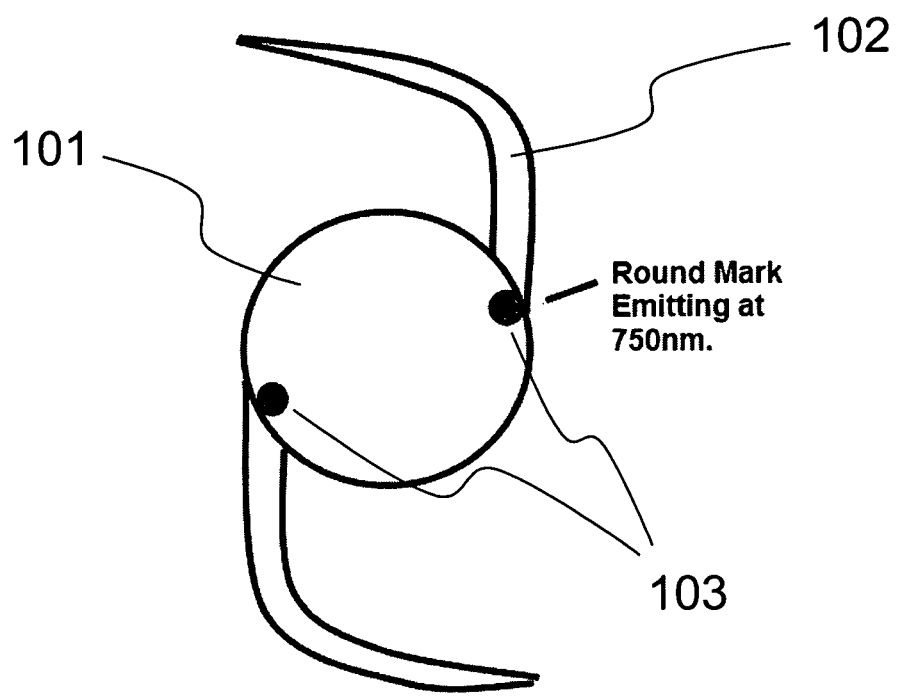
Figure 2A:
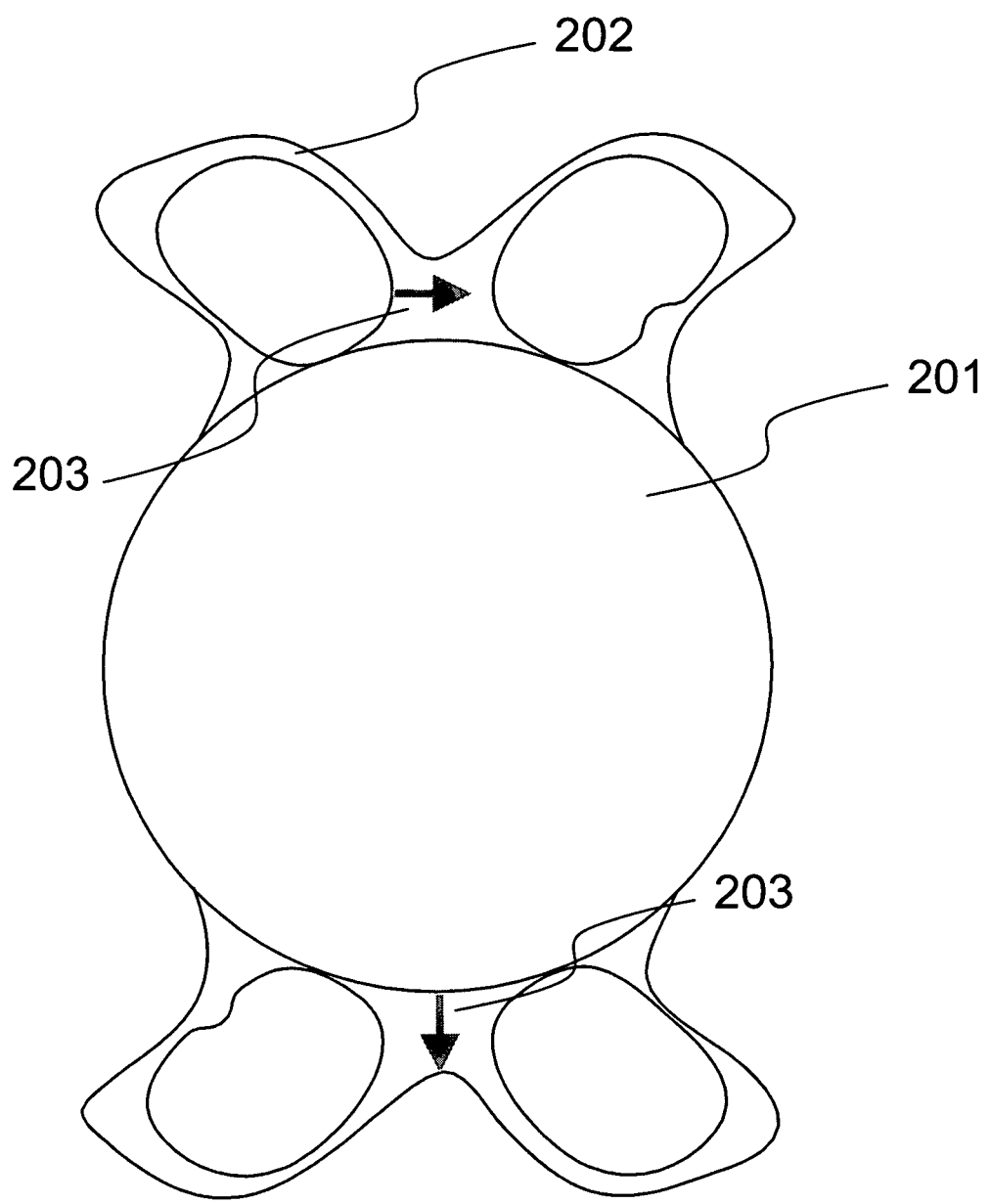
FIG. 2A-B illustrate an intraocular lens with a central lens optic, a pair of haptics and marks on the haptics for indication of orientation and/or location of the lens. When viewed under natural indoor sunlight, the marks (203) show relatively light color with no fluorescence (FIG. 2A), and when viewed under stimulation, e.g., 800 nm, the marks show much brighter color (FIG. 2B)
Figure 2B:
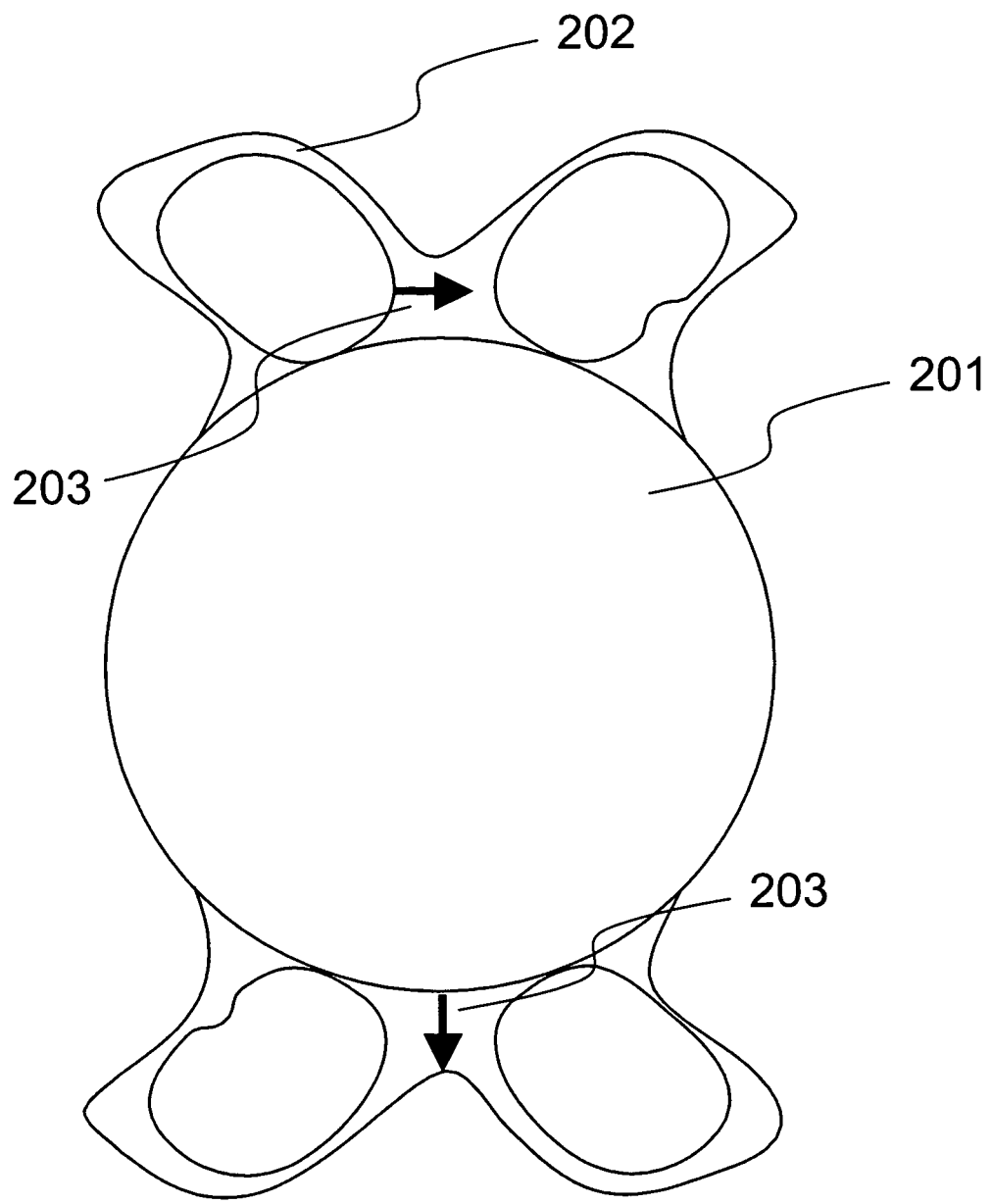

Such contrast is illustrated in FIGS. 1A-B and 2A-B. For instance, the marks (103) show light color under natural light (FIG. 1A) and bright color and fluorescence under UV (FIG. 1B). Likewise, the marks (203) on the haptics (202) have relative light color under natural light (FIG. 2A) but the color is much brighter under stimulation, e.g., 800 nm (FIG. 2B).

If the quantum dot emission is within the visible spectrum, the emission can be easily seen by the human eye alone or with further aid by a microscope. If the quantum dot emission is within the NIR or SWIR spectrum, the emission can be detected by solid state Indium Gallium Arsenide (InGaAs) and/or extended range CCD or CMOS imaging cameras and imaging systems. If the quantum dot emission is within the UV spectrum, the emission can be detected by UV spectroscopy and CCD or CMOS cameras/imaging systems with UV range capabilities.

The brightness of quantum dot emissions under "stimulation" are more than 10-20 times brighter than the "stimulated" emission from fluorescent dye. This greater brightness makes the markings with quantum dots more easily seen both directly and indirectly. The brighter markings may be seen through the pupil and/or by transillumination, through the iris tissue itself, as well as around the pupil by indirect reflection and/or diffraction.

The brighter markings may be seen directly through the pupil. The bright quantum dot markings can be seen by transillumination, through the iris tissue itself. The bright light from a quantum dot mark can be seen indirectly, by reflection and/or diffraction around the edge of the pupil or opaque ocular tissue.

The longevity of quantum dots stimulated emissions are between 30,000-50,000 hours (or 3.5-6 years). Most fluorescent dyes have far shorter emission lives due to degradation, from photo bleaching or protein conjugation, which limits their functional usefulness as a marker over time. In some embodiments, therefore, the quantum dots in the lens of the present disclosure have are able to produce stimulated emission at least 1 year, or alternatively at least 2 years, or 3 years after implantation.

However, an intraocular lens using quantum dot markings will be able to be detected for many years after implantation in the eye due to the longer emission life of quantum dots.

Quantum dot emission is greatly intensified by use of a stimulating light. Each quantum dot has it's own optimal stimulating frequency which can lie in the UV, visible, NIR and SWIR spectrum.

A major advantage unique to quantum dots is the broad spectral separation of stimulating frequency and emission frequency. Since ocular tissues are reflective, a broader separation of the stimulating and emitting frequency greatly enhances the signal to noise ratio. A higher signal to noise ratio reduces the chance that the marking will be undetectable or mistaken for reflected stimulating frequency.

In contrast, fluorescent dyes generally have absorption and emission frequencies which are much closer to each other and frequently overlap one and another. Marks made with dyes have greater detection problems due to this spectral ambiguity.

The specific emission frequency of quantum dots can be tuned by selection of core material as well as by the overall size and shape of the quantum dot. Quantum dots composed of the same core material, but with different core sizes, emit light of different wavelengths. For example, a 20 nm quantum dot will emit in the NIR spectrum, a 10 nm quantum dot will emit in the red spectrum, a smaller 5 nm quantum dot will emit in the blue spectrum, a 3 nm quantum dot will emit in the UV spectrum, and all of them can be made out of the same material.

The size of a quantum dot therefore depends on the desired emission wavelength. They can range in size from 100 nm and smaller, with most typical applications in the range of 50 nm and smaller. In some embodiments, therefore, the quantum dots included in the marks on the IOL have a size from about 2 nm to about 100 nm. In some embodiments, the quantum dots have a size that is at least about 2 nm, 3 nm, 4 nm, 5 nm, 6 nm, 7 nm, 8 nm, 9 nm, 10 nm, 11 nm, 12 nm, 13 nm, 14 nm, 15 nm, 20 nm, 25 nm, 30 nm, 40 nm, 50 nm, 60 nm, 70 nm, 80 nm or 90 nm. In some embodiments, the quantum dots have a size that is not greater than about 90 nm, 80 nm, 70 nm, 60 nm, 50 nm, 40 nm, 30 nm, 25 nm, 20 nm, 15 nm, 14 nm, 13 nm, 12 nm, 11 nm, 10 nm, 9 nm, 8 nm, 7 nm, 6 nm, 5 nm, 4 nm, or 3 nm. In some embodiments the quantum dots have a size between about 2 nm and about 10 nm, or between about 20 nm and about 100 nm, or between about 15 nm and about 50 nm, or between about 2 nm and about 5 nm, or between about 15 nm and about 30 nm.

In one embodiment, the quantum dots can be stimulated to produce an emission wavelength of between 300 nm and 2,000 nm, between 750 nm and 2000 nm, between 600 nm and 749 nm, between 561 nm and 599 nm, between 500 nm and 560 nm, between 400 nm and 499 nm, or between 300 nm and 399 nm.

Various building block materials can be used to produce quantum dots including, without limitation, Cadmium, Selenium, Gold, Silver, Gallium, Indium, Silicon, Germanium, Copper, Lead, Arsenic, Zinc, Iron, as well as from the Lanthanide family of elements.

There are a growing number of quantum dots which are commercially available offering a non-toxic core. Cadmium free or heavy metal free quantum dots are particularly well suited for use in medical devices in general and intraocular lenses in particular.

The core of a quantum dot may be encapsulated by a protective shell designed to insulate it from oxidation and to prevent leakage of the core itself. Zinc Sulfide and various other materials are used to produce a shell around a quantum dot.

Commercially available quantum dots offer various other coatings which can be custom designed for their unique applications. Functional grafting, ligands, and other surface modifiers can be used for a variety of reasons including: improved nano-dispersion, reduced agglomeration, and improved reactivity and chemical bonding with the host substrate or polymer.

It is to be understood that, even though the present technology is described with quantum dots as the illustrative example, other types of materials can also be used to form a mark for the purpose of identifying the orientation and/or location of the lens. Such a material, in some embodiments, when stimulated under UV, NIR, IR or SWIR spectrum, generates at least 10 fold, 15 fold, or 20 fold brighter emission than under normal sunlight. Therefore, they can look relatively faint under normal use condition, without interfering with the function of the lens, but are much easier to visualize, either by eye alone or with a sensor, under UV, NIR, IR or SWIR spectrum.

Intraocular Lenses

The intraocular lens of the present disclosure, in some embodiments, comprises a central lens optic and a mark that includes quantum dots or other materials as described above. In some embodiments, the mark is at a location and/or in a shape suitable to indicate the orientation or location of the lens.

For identification of the orientation of an IOL, it is contemplated that the mark has a shape that appears different when viewed from front and back. In one aspect, the mark is asymmetrical. In another aspect, the mark includes multiple signals that form a pattern which is not symmetrical. A non-limiting example of such a mark is shown in FIG. 2A-B as marks 203.

For identification of the location of an IOL, in another aspect, the mark only needs to be visible. For instance, the marks 103 in FIG. 1A-B form a symmetric pattern but nevertheless are adequate to identify the location of the IOL.

In some embodiments, multiple marks can be used to form a pattern. Such a pattern can include, but are not limited to, one or more of dots, line segments, arcs, squares, cross-hatching, ovals, circles, polygons with three or more sides, and so on. Some patterns can reside within other patterns. Some patterns can overlap with other patterns. Patterns can be formed using one or more types of quantum dots and/or color materials.

In some embodiments, multiple textures can be used in a mark or pattern, such as two, three, or more textures. Such textures may include, but are not limited to, smooth, hard, soft, bristled, rubbery, fuzzy, wavy, bumpy, and the like. Textures may be formed using one or more materials.

In some embodiments, multiple colors, multiple patterns, or multiple textures can be used, including, but not limited, two or more colors, two or more patterns, or two or more textures. In some cases, two or more colors can be used with two or more patterns, or two or more colors can be used with two or more textures, or two or more patterns can be used with two or more textures. In some cases, two or more colors can be used with two or more patterns and two or more textures.

In some embodiments, the mark is disposed on a haptic that extends from the central lens optic. As shown in FIG. 2A-B, the marks (203) are located on the haptics (202) which are connected with the central optic (201). In some embodiments, the mark is disposed on the central lens optic (as illustrated in FIG. 1A-B, with the marks 103 located on lens 101, not on the haptics 102).

In some embodiments, it is contemplated that a sufficient number of quantum dots are present in the mark so that the mark is visible. Nevertheless, as the mark can be seen by eyes alone or by a sensor, such a requirement varies. For detection by a sensor, it is believe that an extremely small number of quantum dots (e.g., greater than 10, 50, 100, 1,000, 10,000 or more) are needed. For detection by naked eyes, the number of quantum dots required is larger and can be ascertained with methods known in the art, which can be, for instance, at least $10^6$, $10^7$, $10^8$, or $10^9$ or more.

Figure 3:
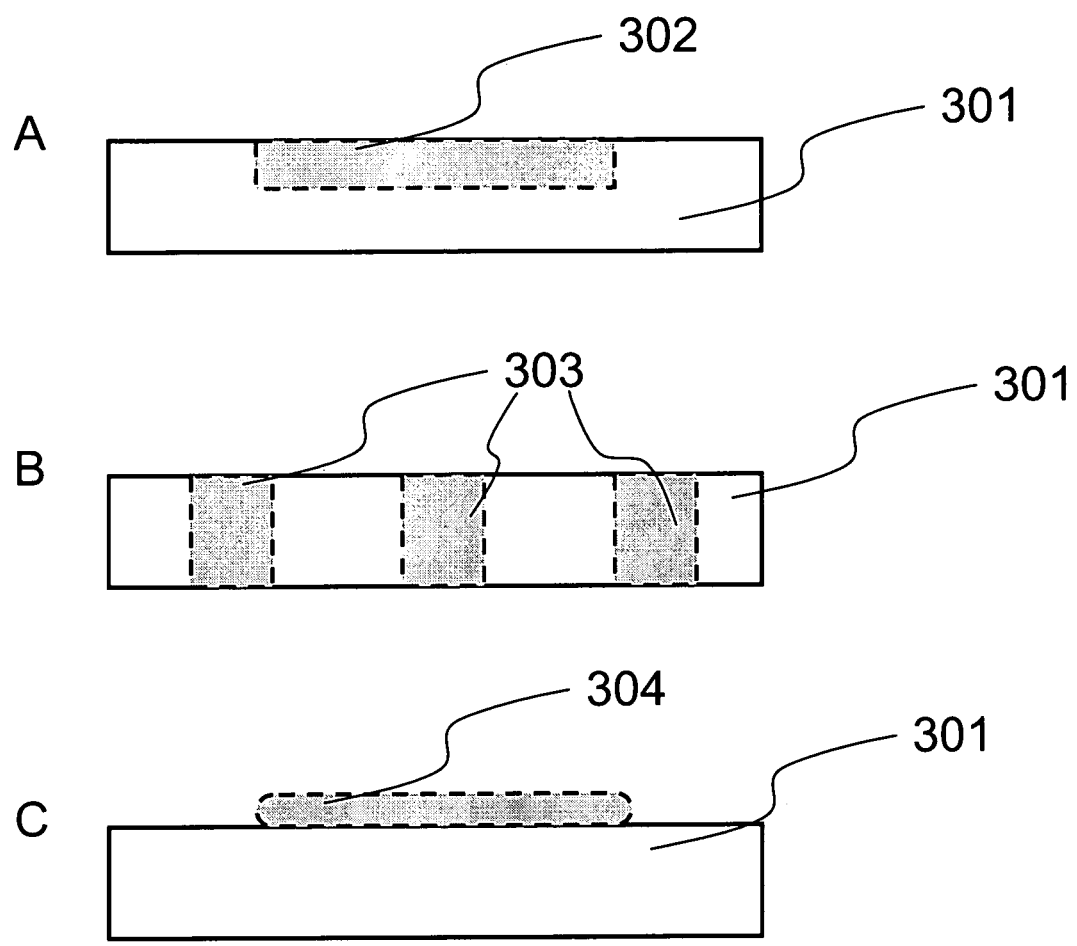
FIG. 3A-C illustrate different ways the quantum dots or the mark containing the dots are disposed on the intraocular lens.

In some embodiments, the mark can be disposed above the surface of the lens optic or haptic (see, e.g., mark 304 above the lens or haptic 301 in FIG. 3C). In some embodiments, the mark is embedded in the lens or haptic, or a layer on the lens or haptic, as illustrated in FIG. 3A, which the mark 302 is disposed in a depression of the lens or haptic 301. In some embodiments, the lens or haptic include a plurality of small depressions or holes to hold the quantum dots of the mark. FIG. 3B illustrates such an embodiment, in which the quantum dots in the holes of the lens or haptic 301, to form a mark 303.

In some embodiments, the mark is in a layer that is also filled with a second quantum dot species characterized by a different emission wavelength, in order to create a mark which can produce two emissions either simultaneously if both species of quantum dot have the same or similar stimulating frequency, or sequentially should the quantum dots have different stimulating frequencies. Therefore, in some embodiments, the intraocular lens further includes one or more additional "marking" layer(s), containing a second species of quantum dot characterized by a different emission wavelength and/or different "stimulating wavelength".

In some embodiments, the layer is also filled with one or more colorants, including, but not limited to copper phthalocyanine, D&C Violet No. 2, or D&C Green No. 6 and titanium dioxide.

Methods of Use

Methods for using an intraocular lens of the present disclosure are also provided. Such methods, in one embodiment, entail detecting the mark containing the quantum dots, when they are stimulated to generate an emission. Under the guidance of the detected mark, one can then identify the orientation and/or location of the lens. Upon identification of the orientation and/or location of the lens, a user, such as a medical professional, can then carry out implantation of the lens or adjustment of the lens if the lens is already implanted.

The emission from an IOL with quantum dot mark can be used to identify the orientation of such an IOL not only when the mark can be seen directly, but also when the mark is not visible to naked eyes directly, such as when the lens is implanted and covered behind the iris.

For example, when the area of the IOL which contains the quantum dot orientation marking is covered by the iris, the emission light from the quantum dots can be detected by its direct transmission through the iris tissue by virtue of the brightness of the emission light or its frequency.

If the quantum dots are tuned to emit in the dark red, NIR, or SWIR wavelengths, these wavelengths can penetrate through the iris and other ocular tissues and be detected by infrared detecting equipment. A solid state InGaAs, CCD, or CMOS camera can be used in conjunction with a slit lamp or microscope to detect the emissions from quantum dot marks.

If the quantum dots are tuned to emit in the visible light spectrum, the emission may still be able to either penetrate through the iris, depending on the color of patients iris, iris thickness and other features, and/or be detected by reflection and diffraction around the pupil of the iris.

The detection of the IOL quantum dot emission light can be visualized using by a variety of means depending on the emission wavelength. Due to the brightness of quantum dot emission, if the emission wavelength is in the visible spectrum, a simple microscope can be used.

If the mark's emission level is of low intensity due to being covered by iris or other opaque ocular tissue, a device optimized to detect the emission wavelength of the quantum dot, such as InGaAs, CCD, or CMOS cameras/imaging systems with special filters and acquisition software can be employed.

The well-defined and diverse specific emission wavelengths of quantum dots can be used singly or in combination to create a color code for a more intelligent mark. Using multiple species of quantum dots with a differing emission wavelengths and/or color pigments, additional parameters of the intraocular lens can be identified, such as the magnitude of astigmatic correction.

A mixture of different kinds of quantum dots can be used to mark the lens in order to convey the power of astigmatic correction as well as for enhanced detection when the mark is covered by the iris. Use of quantum dots with different emission wavelengths can create marks which can color code data about the optical correction such as the magnitude of toric correction. Use of a quantum dots which transmits in the NIR or SWIR spectrum would enable detection in the event of the mark being covered by the iris, when viewed with a InGaAs, CCD, or CMOS solid state cameras and/or other SWIR/NIR imaging equipment, i.e. filters and specialized software.

For example, a toric correcting intraocular lens with a +1.00 diopter astigmatic correction can be marked with a quantum dot with a emission of 450 nm to produce a blue color marking when stimulated. Likewise, a toric lens with a +2.00 diopter astigmatic correction can be marked with a quantum dot of 540 nm emission to produce a green color marking when stimulated. A toric lens with a +3.00 diopter astigmatic correction, further, can be marked with a quantum dot of 620 nm emission to produce a red color marking when stimulated.

To identify the whether there is an addition half diopter power, i.e., +1.50, an additional quantum dot with a different stimulating and emitting wavelength, such as one with a yellow emission, can be added to the marking layer.

In such a case, the user can first search for the whole power of astigmatic correction using a first stimulating wavelength and then search for the half power using a second stimulating wavelength. If the user detects the yellow emission, then this would confirm there was a +0.5 diopter additional power of astigmatism correction, in this case, +1.50 diopter. If no yellow emission was detected, then this would confirm the diopter power to be a whole value, in this case, +1.00 diopter.

Methods of Fabrication

The present disclosure also provides methods of fabrication. The fabrication, in one embodiment, begins with providing an object, namely a intraocular lens and polymerizing at least one first monomer containing nano-sized quantum dots to form a "marking" layer that contacts the object on its surface.

Micro-deposition MEMS equipment such as made by FUJI Dimatix Inkjet or BIODOT can be used to accurately deposit micro-drops of uncured quantum dot filled polymer to either the flat surface on the intraocular lens or to a micro-depression in the intraocular lens. The deposited uncured quantum dot filled polymer would then be polymerized and become integrated into the IOL.

In some embodiments, the nano-sized semiconductor quantum dots are dispersed in (co-)monomers or uncured (co-)polymers. Such dispersions may also optionally include colorant particles. Conventional mixing techniques may be employed to prepare dispersions, including, but not limited to, closed-rotor, ultrasound, rotor-stator, colloid mill, homogenizers, and microfluidizer processors.

Matching the type of quantum dot to the particular polymer application may also improve homogeneity and other qualities of the dispersion. For example, quantum dots with particular type of functional groups attached to their outer surface may be paired with compatible co-monomers and/or functional groups.

For example, the starting point may be a blank disc with drilled spaces or blind holes which could be filled with uncured liquid dispersion of (co-)monomers or uncured (co-)polymers, filled with nano-sized semiconductor quantum dots, cross-linkers, and initiators. Once the spaces have been filled, the uncured mixture would be polymerized, thereby integrating the marking layer into the blank disc. This marked disc can then be used to create a finished intraocular lens using micro-milling and micro-lathing techniques.

Another approach would be start with an intraocular lens and deposit uncured liquid dispersion of (co-)monomers or uncured (co-)polymers, nano-sized semiconductor quantum dots, cross-linkers, and initiators, either onto the surface of the intraocular lens or into a small depressions milled into the intraocular lens. The deposited uncured mixture would be polymerized, thereby integrating the marking layer into the intraocular lens.

The polymers or copolymers used may be obtained by polymerization of various monomers commonly used in the production of IOLs, such as methyl methacrylate (MMA) or by copolymerization of various hydrophilic or hydrophobic comonomers, such as 2-hydroxyethyl methacrylate (HEMA), in various combinations thereof. A copolymer with HEMA and MMA repeat units may be referred to as pHEMA-MMA.

Any (co-)monomer or uncured copolymer that is suitable for intraocular lenses/haptics may be used, including, but not limited to, those used in producing hydrophilic, hydrophobic, and silicone-based optics/haptics.

Examples of hydrophilic (co-)monomers include, but are not limited to, 2-hydroxyethylacrylate, 2-hydroxyethylmethacrylate, ethoxyethylmethacrylate, and acrylamide.

Examples of hydrophobic (co-)monomers include, but are not limited to, phenylethyl methacrylate, phenylethyl acrylate, ethyl acrylate, ethyl methacrylate, glyceralmethacrylate, diacetoneacrylamide, lauryl methacrylate, butyl methacrylate, 2-ethylhexylmethacrylate, vinyl hydroxyacetate, vinyl hydroxyproprionate, vinyl hydroxybutyrate, and N-vinyl lactams.

Other examples of (co-)monomers and uncured (co-)polymers include, but are not limited to, phenylethyl acrylate, phenylethyl methacrylate, N,N-dimethylacrylamide, methacrylic acid, N-vinyl pyyolidone, tris-(trimethylsiloxysilyl) propylvinyl carbonate, N-carboxyvinyl ester, poly[dimethyldoloxy]di[silylbutanol]bis[vinyl carbamate], polyvinyl pyrrolidone, polydimethylsiloxane, and fluoroether macromers.

Polymerization may be started using thermal initiators, such as azobisisobutyronitrile (AIBN), benzoyl peroxide, potassium persulfate, ammonium persulfate, benzophenone, methacryloyloxy benzophenone and N,N-dimethylaminoethyl methacrylate, and the like, used either as sole agents or in various combinations thereof.

Photoinitiators may also be employed on thin films and when faster polymerization times are sought. These agents include, but are not limited to, anthraquinones, methylanthraquinones, camphoquinone tertiary amine hybrid, benzoin ethyl ether, and the like. Examples of photoinitators also include, but are not limited to, 1-[4-(2-hydroxyethyoxy)-phenyl]-2-hydroxy-2-methyl-1-propane-1-one (IRGACURE 2959), phenyl-bis(2,4,6-trimethylbenzoylphosphine oxide) (IRGACURE 819), and the like.

The (co-)polymers may be subjected to inter-molecular crosslinking, to adjust their physical strength and water content. Crosslinking agents may include, but are not limited to, acrylate or acrylamide-based compounds, for example, ethylene glycol dimethacrylate (EGDMA), diethylene glycol bismethacrylate, butanediol diacrylate, fluoralkyl methacrylate, or N,N-methylene bis(acrylamide), and the like. The amount of the crosslinking agent used may be the range of 0.01-2.0 wt % based on the total weight of the monomers, and may be preferably in the range of 0.05-1.5 wt %.

Although various polymerization techniques may be employed, ultraviolet (UV) curing with high energy UV sources, such as, but not limited to, medium pressure mercury lamps, may provide cure times of, for example, a few seconds to a few minutes.

Undesired surface morphologies, such as ripples or bubbles, may be reduced or eliminated by curing the substrate in an oxygen deprived environment. Such an oxygen deprived environment may be provided by any suitable method, including, but not limited to, use of $CO_2$ gas blanketing or purging. Surface curing may also be reduced by such methods as, for example, simultaneously filtering both UVC and UVB wavelengths of ultraviolet light with optical filters placed between the UV lamp and the substrate.

WORKING EXAMPLES

Example 1

7.5 mL of 2-hydroxyethyl methacrylate (HEMA), 2.5 mL ethoxyethyl methacrylate (EOEMA), and sufficient ethylene glycol dimethacrylate (EGDMA) to provide a 1.5 wt % loading were mixed together in a propeller mixer for 30 minutes. Sufficient amounts of IRGACURE® 2959 (Ciba/BASF) and IRGACURE® 819 (Ciba/BASF) photoinitiators were added to the mixture to provide 1 wt % loadings of each. The mixture was mixed for 30 minutes. Sufficient nano-sized quantum dot, with a 750 nm emission frequency and 400 m stimulation frequency, was added to the mixture to provide a 0.3 wt % loading and then stirred with a propeller mixer for 10 minutes.

The mixture was then processed using a Q-sonic sonicator with a ¾ inch solid tip probe at 40-60% power for 1 hour. A water ice bath was used to maintain the temperature.

The processed mixture was then deposited into two cylindrical depressions which were previously milled into the intraocular lens. The cylindrical depressions have a radius of 200 microns and a depth of 120 microns. The cylindrical depressions were filled with the liquid quantum dot filled copolymer. The intraocular lens was placed beneath a medium pressure mercury lamp, 11 inches in length and rated at 300 watts/inch (JeLight Inc., Irvine, Calif.). An infra-red mirror was positioned 2 inches beneath the lamp and 5 inches above the substrate. The intraocular lens was exposed to ultraviolet radiation for 2-3 minutes.

The marked intraocular lens was hydrated overnight in saline solution in order to transform into a foldable hydrogel intraocular lens.

The hydrated foldable intraocular lens was stimulated with 400 nm light and a orange-red fluorescence was observed. The stimulated emission was also able to be detected with both a CCD and NIR/SWIR camera.

The contents of the articles, patents, and patent applications, and all other documents and electronically available information mentioned or cited herein, are hereby incorporated by reference in their entirety to the same extent as if each individual publication was specifically and individually indicated to be incorporated by reference.

Applicants reserve the right to physically incorporate into this application any and all materials and information from any such articles, patents, patent applications, or other physical and electronic documents.

The disclosures illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claims. Thus, it should be understood that although the present disclosure has been specifically disclosed by preferred embodiments and optional features, modification and variation of the disclosures embodied therein herein disclosed may be resorted to by those skilled in the art, and that such modifications and variations are considered to be within the scope of this disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein. Other embodiments are within the following claims. In addition, where features or aspects of the disclosure are described in terms of Markush groups, those skilled in the art will recognize that the disclosure is also thereby described in terms of any individual member or subgroup of members of the Markush group.

What is claimed is:

1. An intraocular lens comprising (a) a central lens optic and (b) a mark disposed on the central lens optic, the mark comprising a plurality of nano-sized particles of semi-conductor nanocrystals, defined as quantum dots;
   wherein the intraocular lens is implanted in an area of the eye selected from the group consisting of the anterior chamber, the iris plane, the ciliary sulcus space, the posterior chamber, and the capsular bag; and
   wherein said mark does not contact the retinal cells of the eye.

2. An intraocular lens comprising (a) a central lens optic and (b) a mark disposed on a haptic projecting outwardly from the central lens optic, the mark comprising a plurality of nano-sized particles of semi-conductor nanocrystals, defined as quantum dots.

3. The intraocular lens according to claim 1 or claim 2, wherein the quantum dots, when stimulated, produce an emission wavelength between 750 nm and 2,000 nm.

4. The intraocular lens according to claim 1 or claim 2, wherein the quantum dots, when stimulated, produce an emission wavelength between 600 nm and 749 nm.

5. The intraocular lens according to claim 1 or claim 2, wherein the quantum dots, when stimulated, produce an emission wavelength of between 561 nm and 599 nm.

6. The intraocular lens according to claim 1 or claim 2, wherein the quantum dots, when stimulated, produce an emission wavelength of between 500 nm and 560 nm.

7. The intraocular lens according to claim 1 or claim 2, wherein the quantum dots, when stimulated, produce an emission wavelength of between 400 nm and 499 nm.

8. The intraocular lens according to claim 1 or claim 2, wherein the quantum dots, when stimulated, produce an emission wavelength of between 300 nm and 399 nm.

9. The intraocular lens according to claim 1 or claim 2, wherein the mark comprises two or more different kinds of quantum dots which have different stimulated emission wavelengths.

10. The intraocular lens according to claim 1 or claim 2, wherein the mark further comprises one or more color pigments.

11. The intraocular lens according to claim 10, wherein the one or more color pigments are selected from the group consisting of copper phthalocyanine, violet dye, green dye, and titanium dioxide.

12. The intraocular lens according to claim 10, wherein the mark is disposed on the haptic.

13. The intraocular lens of claim 1 or claim 2, wherein the mark is disposed in a pattern selected from the group consisting of dots, lines, circles, triangles, bars, letters and numbers.

14. The intraocular lens according to claim 1 or claim 2, wherein the quantum dots, when stimulated, produce an emission wavelength of between 300 nm and 2,000 nm.

* * * * *